United States Patent
Tanaka

(10) Patent No.: US 9,439,425 B2
(45) Date of Patent: Sep. 13, 2016

(54) PLANT DISEASE CONTROL COMPOSITION AND PLANT DISEASE CONTROL METHOD

(71) Applicant: Sumitomo Chemical Company, Limited, Tokyo (JP)

(72) Inventor: Soichi Tanaka, Tokyo (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/406,953

(22) PCT Filed: Jun. 6, 2013

(86) PCT No.: PCT/JP2013/066285
§ 371 (c)(1),
(2) Date: Dec. 10, 2014

(87) PCT Pub. No.: WO2013/187457
PCT Pub. Date: Dec. 19, 2013

(65) Prior Publication Data
US 2015/0173361 A1    Jun. 25, 2015

(30) Foreign Application Priority Data
Jun. 12, 2012  (JP) .................................. 2012-132601

(51) Int. Cl.
| | | |
|---|---|---|
| *A01N 43/56* | (2006.01) | |
| *A01N 47/16* | (2006.01) | |
| *A01N 35/06* | (2006.01) | |
| *A01N 37/26* | (2006.01) | |
| *A01N 43/40* | (2006.01) | |
| *A01N 43/42* | (2006.01) | |
| *A01N 43/54* | (2006.01) | |

(52) U.S. Cl.
CPC ............... *A01N 43/56* (2013.01); *A01N 35/06* (2013.01); *A01N 37/26* (2013.01); *A01N 43/40* (2013.01); *A01N 43/42* (2013.01); *A01N 43/54* (2013.01); *A01N 47/16* (2013.01)

(58) Field of Classification Search
None
See application file for complete search history.

(56) References Cited

U.S. PATENT DOCUMENTS

| | | |
|---|---|---|
| 6,294,567 B1 | 9/2001 | Hashizume et al. |
| 6,710,062 B1 | 3/2004 | Hayashi et al. |
| 2006/0089390 A1 | 4/2006 | Nishide et al. |
| 2011/0092556 A1 | 4/2011 | Soma |
| 2011/0105489 A1 | 5/2011 | Soma et al. |
| 2011/0177944 A1 | 7/2011 | Gewehr et al. |
| 2014/0128411 A1 | 5/2014 | Ogawa et al. |

FOREIGN PATENT DOCUMENTS

| | | | |
|---|---|---|---|
| JP | 2000-226374 A | 8/2000 | |
| JP | 2000-319270 A | 11/2000 | |
| JP | 2002-316902 A | 10/2002 | |
| JP | WO 2013/008604 | * 1/2013 | ............. A01N 43/40 |
| WO | 2004/039155 A1 | 5/2004 | |

OTHER PUBLICATIONS

Tomlin, C D S (editor), "The Pesticide Manual", Fifteeth Edition, pp. 260-261, 786-787, 960-961, 1008-1009.
Int'l Search Report issued on Jul. 9, 2013 in In'l Application No. PCT/JP2013/066285.
Office Action issued Oct. 30, 2015 in NZ App No. 702836.
Office Action issued Dec. 3, 2015 in AU Application No. 2013275292.
Extended Search Report issued Dec. 4, 2015 in EP Application No. 13803992.0.
Notification of Reasons for Refusal issued Apr. 5, 2016 in JP Application No. 2012132601.
Examiner's Report issued Mar. 20, 2016 in CL Application No. 3328-2014.

* cited by examiner

Primary Examiner — Samantha Shterengarts
(74) *Attorney, Agent, or Firm* — Panitch Schwarze Belisario & Nadel LLP

(57) ABSTRACT

A composition containing a compound represented by formula (I) and at least one compound selected from the group consisting of pyriofenone, metrafenone, cyflufenamid, quinoxyfen, and proquinazid

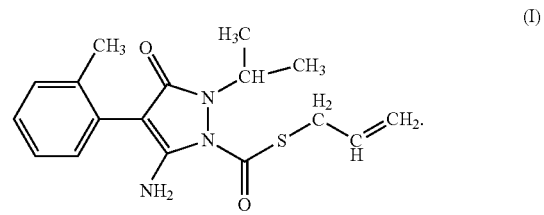

The composition has excellent control effect against plant diseases.

15 Claims, No Drawings

PLANT DISEASE CONTROL COMPOSITION AND PLANT DISEASE CONTROL METHOD

CROSS-REFERENCE TO RELATED APPLICATION

This application is a Section 371 of International Application No. PCT/JP2013/066285, filed Jun. 6, 2013, which was published in the Japanese language on Dec. 19, 2013, under International Publication No. WO 2013/187457 A1, and the disclosure of which is incorporated herein by reference.

TECHNICAL FIELD

The present invention relates to plant disease control compositions and methods for controlling plant diseases.

BACKGROUND ART

A compound represented by formula (I) has been known (see, for example, Patent Document 1).

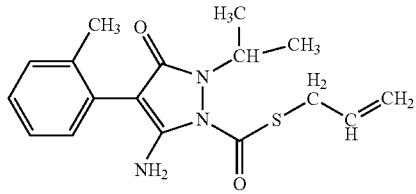
(I)

Moreover, many compounds have been known as an active ingredient of a plant disease control composition (see, for example, Patent Documents 2 and 3 and Non-Patent Document 1).

PRIOR ART DOCUMENTS

Patent Documents

Patent Document 1: JP-A-2000-226374
Patent Document 2: WO 2004/039155 A
Patent Document 3: JP-A-2000-319270

Non-Patent Document

Non-Patent Document 1: The Pesticide Manual—15th edition (published by BCPC) ISBN 1901396188

DISCLOSURE OF THE INVENTION

Problems to be Solved by the Invention

An object of the present invention is to provide a composition showing an excellent control effect against plant diseases.

Means for Solving the Problems

The present inventors intensively studied so as to find a composition having an excellent control effect against plant diseases and have found that a composition comprising a compound represented by formula (I) given below and at least one compound selected from the group consisting of pyriofenone, metrafenone, cyflufenamid, quinoxyfen, and proquinazid has an excellent control effect against plant diseases, having accomplished the present invention.

Specifically, the present invention includes the following configurations.

[1] A plant disease control composition comprising a compound represented by formula (I) and at least one compound selected from Group A,

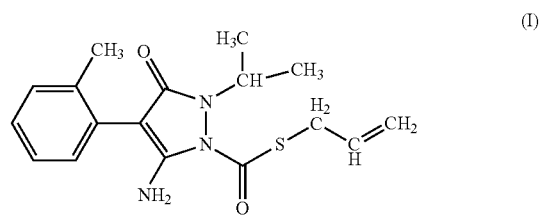 [SMILES: C=CCSC(=O)n1c(N)c(-c2ccccc2C)c(=O)n1C(C)C]
(I)

Group A: the group consisting of pyriofenone, metrafenone, cyflufenamid, quinoxyfen, and proquinazid.

[2] The plant disease control composition according to [1], wherein the weight ratio of the compound represented by formula (I) to the at least one compound selected from Group A is from 1:100 to 100:1.

[3] A method for controlling plant disease, the method comprising a step of applying effective amounts of a compound represented by formula (I) and at least one compound selected from Group A to a plant, a seed of a plant, or a soil where a plant is to be cultivated,

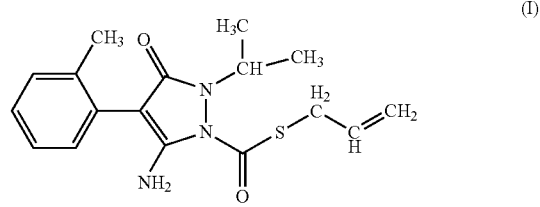 [SMILES: C=CCSC(=O)n1c(N)c(-c2ccccc2C)c(=O)n1C(C)C]
(I)

Group A: the group consisting of pyriofenone, metrafenone, cyflufenamid, quinoxyfen, and proquinazid.

[4] The method for controlling plant disease according to [3], wherein the weight ratio of the compound represented by formula (I) to the at least one compound selected from Group A is from 1:100 to 100:1.

[5] Use of a combination of a compound represented by formula (I) and at least one compound selected from the group consisting of pyriofenone, metrafenone, cyflufenamid, quinoxyfen, and proquinazid, for controlling plant disease.

MODE FOR CARRYING OUT THE INVENTION

The plant disease control composition of the present invention (hereafter referred to as the present invention composition) comprises a compound represented by formula (I) (hereinafter referred to as the present compound (I)) and at least one compound selected from Group A (hereinafter referred to as the present compound A).
Group A: the group consisting of pyriofenone, metrafenone, cyflufenamid, quinoxyfen, and proquinazid.

The present compound (I) is a compound disclosed in JP-A-2000-226374, for example, and can be produced by the method disclosed in this publication.

Pyriofenone, which is used for the present invention, is a compound disclosed in WO 2004/039155 A, for example, and can be produced by the method disclosed in this publication.

Metrafenone, cyflufenamid, quinoxyfen, and proquinazid are publicly known compounds, are disclosed in pages 786, 261, 1008, and 961 of "THE PESTICIDE MANUAL—15th EDITION (published by BCPC) ISBN 1901396188", respectively, for example, and can be produced by publicly known methods.

The weight ratio of the present compound (I) to the present compound A in the present invention composition is usually from 100:1 to 1:100, preferably from 10:1 to 1:10, and more preferably from 5:1 to 1:5.

Although the present invention composition may be a mixture itself of the present compound (I) with the present compound A, the present invention composition is usually prepared by mixing the present compound (I), the present compound A, an inert carrier such as a solid carrier or a liquid carrier and, as necessary, adding a surfactant or other formulation additives, and then formulating the mixture into a dosage form such as an oil solution, an emulsifiable concentrate, a suspension concentrate, a wettable powder, a water dispersible granule, a dust, or a granule. Such formulations can be used as it is or with addition of other inert components as an agent for controlling plant diseases.

In the present invention composition, the present compound (I) and the present compound A are contained usually in an amount of 0.1 to 99% by weight, preferably 0.2 to 90% by weight, and more preferably 1 to 80% by weight, in total.

Examples of the solid carrier to be used for formulation include fine powders and granules of minerals such as kaolin clay, attapulgite clay, bentonite, montmorillonite, acidic white clay, pyrophylite, talc, diatomaceous earth, and calcite, natural organic substances such as corncob flour and walnut shell flour, synthetic organic substances such as urea, salts such as calcium carbonate and ammonium sulfate, and synthetic inorganic substances such as synthetic hydrated silicon oxide. Examples of the liquid carrier include aromatic hydrocarbons such as xylene, alkylbenzene and methyl naphthalene, alcohols such as 2-propanol, ethylene glycol, propylene glycol and ethylene glycol monoethyl ether, ketones such as acetone, cyclohexanone and isophorone, vegetable oils such as soybean oil and cotton oil, petroleum-based aliphatic hydrocarbons, esters, dimethylsulfoxide, acetonitrile, and water.

Examples of the surfactant include anionic surfactants such as alkyl sulfate ester salts, alkylaryl sulfonates, dialkyl sulfosuccinates, polyoxyethylene alkylaryl ether phosphate ester salts, lignosulfonates and naphthalene sulfonate formaldehyde polycondensates, nonionic surfactants such as polyoxyethylene alkylaryl ethers, polyoxyethylene alkylpolyoxypropylene block copolymers and sorbitan fatty acid esters, and cationic surfactants such as alkyltrimethylammonium salts.

Examples of the formulation additives include water-soluble polymers such as polyvinyl alcohol and polyvinyl pyrrolidone, polysaccharides such as gum arabic, alginic acid and salts thereof, CMC (carboxymethyl cellulose) and xanthan gum, inorganic substances such as aluminum magnesium silicate and alumina sol, preservatives, colorants, and stabilizers such as PAP (acidic isopropyl phosphate) and BHT.

The present invention composition can also be prepared by formulating the present compound (I) and the present compound A separately by the method described above, then diluting them with water as necessary, and then mixing the respective formulations or their dilutions.

The present invention composition may further comprise one or more other fungicides and/or insecticides.

The present invention composition is used for controlling a plant disease by applying it to a plant or a soil where a plant is to be cultivated.

Examples of a plant disease that can be controlled by the present invention include the following.

Rice diseases: rice blast (*Magnaporthe oryzae*), brown spot (*Cochliobolus miyabeanus*), sheath blight (*Rhizoctonia solani*), bakanae disease (*Gibberella fujikuroi*);

Diseases of barley, wheat, oat and rye: powdery mildew (*Erysiphe graminis, Blumeria graminis*), head blight (*Fusarium graminearum, F. avenacerum, F. culmorum, F. asiaticum, Microdochium nivale*), rust (*Pucciniastriiformis, P. graminis, P. recondite, P. hordei*), snow mold (*Typhula sp., Micronectriella nivalis*), loose smut (*Ustilago tritici, U. nuda*), bunt (*Tilletia caries*), eyespot (*Pseudocercosporella herpotrichoides*), scald (*Rhynchosporium secalis*), leaf blotch (*Septoria tritici*), glume blotch (*Leptosphaeria nodorum*), net blotch (*Pyrenophora teres* Drechsler);

Citrus diseases: black spot (*Diaporthe citri*), scab (*Elsinoe fawcetti*, fruits rot (*Penicillium digitatum, P. italicum*);

Apple diseases: blossom blight (*Monilinia mali*), powdery mildew (*Podosphaera leucotricha*), Alternatia blotch (*Alternaria* alternate apple pathotype), scab (*Venturia inaequalis*), bitter rot (*Colletotrichum acutatum*);

Pear diseases: scab (*Venturia nashicola, V. pirina*), black spot (*Alternaria* alternate Japanese pear pathotype), rust (*Gymnosporangium haraeanum*);

Peach diseases: brown rot (*Monilinia fructicola*), scab (*Cladosporium carpophilum*), phomopsis rot (*Phomopsis sp.*);

Grape diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), gray mold (*Botrytis cinerea*);

Persimmon diseases: anthracnose (*Gloeosporium kaki*), leaf spot (*Cercospora kaki, Mycosphaerella nawae*);

Diseases of cucurbits: anthracnose (*Colletotrichum lagenarium*), powdery mildew (*Sphaerotheca fuliginea*), gummy stem blight (*Mycosphaerella melonis*), wilt (*Fusarium oxysporum, phytophthora* rot (*Phytophthora sp.*), damping-off (*Pythium sp.*);

Tomato diseases: early blight (*Alternaria solani*), leaf mold (*Cladosporium fulvum*);

Eggplant disease: brown spot (*Phomopsis vexans*), powdery mildew (*Erysiphe cichoracearum*);

Diseases of cruciferae vegetables: black spot (*Alternaria japonica*), white spot (*Cercosporella brassicae*), club root (*Plasmodiophora brassicae*);

Rapeseed diseases: white stem rot (*Sclerotinia sclerotiorum*), brack spot (*Alternaria brassicae*), powdery mildew (*Erysiphe cichoracearum*), black leg (*Leptosphaeria maculans*);

Welsh onion diseases: rust (*Puccinia allii*);

Soybean diseases: purple stain (*Cercospora kikuchii*), scab (*Elsinoe glycines*), pod and stem blight (*Diaporthe phaseolorum* var. *sojae*), rust (*Phakopsora pachyrhizi*);

Adzuki-bean diseases: gray mold (*Botrytis cinerea*), sclerotinia rot (*Sclerotinia sclerotiorum*);

Kidney bean diseases: gray mold (*Botrytis cinerea*), sclerotinia rot (*Sclerotinia sclerotiorum*), anthracnose (*Colletotrichum lindemthianum*);

Peanut diseases: leaf spot (*Cercospora personata*), brown leaf spot (*Cercospora arachidicola*), southern blight (*Sclerotium rolfsii*);
Pea diseases: powdery mildew (*Erysiphe pisi*);
Potato diseases: early blight (*Alternaria solani*);
Strawberry diseases: powdery mildew (*Sphaerotheca humuli*);
Tea diseases: net blister blight (*Exobasidium reticulatum*), white scab (*Elsinoe leucospila*), gray blight (*Pestalotiopsis* sp.), anthracnose (*Colletotrichum theae-sinensis*);
Cotton diseases: wilt (*Fusarium oxysporum*), damping-off (*Rhizoctonia solani*);
Tobacco diseases: brown spot (*Alternaria longipes*), powdery mildew (*Erysiphe cichoracearum*), anthracnose (*Colletotrichum tabacum*);
Sugar beet diseases: leaf spot (*Cercospora beticola*), leaf blight (*Thanatephorus cucumeris*), root rot (*Thanatephorus cucumeris*), root rot (*Aphanidermatum cochlioides*);
Rose diseases: black spot (*Diplocarpon rosae*), powdery mildew (*Sphaerotheca pannosa*);
Chrysanthemum diseases: leaf blight (*Septoria chrysanthemi-indici*), rust (*Puccinia horiana*);
Diseases of various plants: gray mold (*Botrytis cinerea*), sclerotinia rot (*Sclerotinia sclerotiorum*);
Japanese radish diseases: leaf spot (*Alternaria brassicicola*);
Wheat grass diseases: doller spot (*Sclerotinia homeocarpa*), brown patch and large patch (*Rhizoctonia solani*);
Banana diseases: sigatoka disease (*Mycosphaerella fijiensis, Mycosphaerella musicola, Pseudocercospora musae*).

Examples of the plants to which the present invention composition can be applied are as follows:

Crops: maize, rice, wheat, barley, rye, oat, sorghum, cotton, soybean, adzuki-bean, kidney bean, peanut, buckwheat, sugar beet, rapeseed, sunflower, sugar cane, tobacco, etc.;

vegetables: solanaceae vegetables (eggplant, tomato, green pepper, hot pepper, potato, etc.), cucurbitaceae vegetables (cucumber, pumpkin, zucchini, watermelon, melon, squash, etc.), cruciferae vegetables (Japanese radish, turnip, horseradish, kohlrabi, Chinese cabbage, cabbage, brown mustard, broccoli, cauliflower, etc.), compositae vegetables (burdock, garland *chrysanthemum*, artichoke, lettuce, etc.), liliaceae vegetables (Welsh onion, onion, garlic, and asparagus), umbelliferae vegetables (carrot, parsley, celery, parsnip, etc.), chenopodiaceae vegetables (spinach, Swiss chard, etc.), labiatae vegetables (Japanese mint, mint, basil, etc.), strawberry, sweet potato, Japanese yam, aroid, etc.;

flowers;

foliage plants;

wheat grass;

fruits: pomaceous fruits (apple, common pear, Japanese pear, Chinese quince, quince, etc.), stone fleshy fruits (peach, plum, nectarine, Japanese plum, cherry, apricot, prune, etc.), citrus plants (Satsuma mandarin, orange, lemon, lime, grapefruit, etc.), nuts (chestnut, walnut, hazel nuts, almond, pistachio, cashew nut, macadamia nut, etc.), berry fruits (blueberry, cranberry, blackberry, raspberry, etc.), grape, persimmon, olive, loquat, banana, coffee, date, coconut, etc.; and trees other than fruit trees: tea, mulberry, flowering trees and shrubs, street trees (ash tree, birch, dogwood, *eucalyptus*, ginkgo, lilac, maple tree, oak, poplar, *cercis*, Chinese sweet gum, plane tree, *zelkova*, Japanese arborvitae, fir tree, Japanese hemlock, needle juniper, pine, spruce, and yew), etc.

The aforementioned "plants" may be plants to which resistances have been imparted using a genetic recombination technology.

The method for controlling a plant disease of the present invention (hereinafter referred to as the controlling method of the present invention) is performed by applying effective amounts of the present compound (I) and the present compound A to a plant, a seed of a plant, or a soil where a plant is to be cultivated. Examples of such plants include a foliage and a root. Examples of such a seed of a plant include seeds and bulbs. The bulbs as used herein include scaly bulbs, corms, root stalks, tubers, tuberous roots, and rhizophores.

In the controlling method of the present invention, the present compound (1) and the present compound A may be applied separately at around the same time to a plant, a seed of a plant, or a soil where a plant is to be cultivated, but they are usually applied in the form of the present invention composition because of the convenience in its application.

In the method for controlling of the present invention, examples of the method of applying the present invention composition include foliage treatment, soil treatment, root part treatment, and seed treatment.

Such foliage treatment includes a method of applying the composition to a surface of a plant under cultivation, such as spreading to foliages and spreading to trunks.

Such soil treatment includes spreading on a soil, mixing with a soil, and drug solution injection into a soil.

Such root part treatment includes a method of soaking the whole or a root part of a plant into a drug solution comprising the present compound (I) and the present compound A, and a method of attaching a solid formulation comprising the present compound (I), the present compound A and a solid carrier to a root part of a plant.

Such seed treatment includes application of the present invention composition to a seed or a bulb of a plant to be prevented from a plant disease, specifically, for example, spray treatment by spraying a suspension of the present invention composition in a mist form to a surface of a seed or a surface of a bulb, smear treatment by smearing a wettable powder, an emulsifiable concentrate or a flowable formulation of the present invention composition with an addition of a small amount of water or as it is to a seed or a bulb, immersion treatment by immersing a seed into a solution of the present invention composition for a given time, film-coating treatment, and pellet-coating treatment.

The dose of the present compound (I) and the present compound A in the controlling method of the present invention can vary depending on the kind of the plant to be treated, the kind or the occurrence frequency of the plant disease to be controlled, the dosage form, the treatment period, the treatment method, the treatment site, the climatic conditions, etc. In the case of application to a foliage of the plant or to a soil where a plant is to be cultivated, the total amount of the present compound (I) and the present compound A is usually 1 to 500 g, preferably 2 to 200 g, and more preferably 10 to 100 g, per 1000 $m^2$. The dose of the present compound (I) and the present compound A in the application to seeds, expressed by the total amount of the present compound (I) and the present compound A, is usually 0.001 to 10 g, preferably 0.01 to 1 g, per 1 kg of seeds.

The emulsifiable concentrate, the wettable powder, the flowable formulation, and so on are usually applied by diluting them with water and then spreading. In this case, the concentration of the present compound (I) and the present compound A in total is usually 0.0005 to 2% by weight, preferably 0.005 to 1% by weight. The dust formulation, the granular formulation, and the like are usually applied as it is without diluting them.

EXAMPLES

The present invention is described in more detail below by reference to formulation examples and test examples.

Formulation examples are described below. In the formulation examples, the term "part" indicates "part by weight".

Formulation Example 1

A formulation is obtained by mixing 5 parts of the present compound (I), 5 parts of pyriofenone, 35 parts of a mixture of white carbon and a polyoxyethylene alkyl ether sulfate ammonium salt (weight ratio 1:1), and 55 parts of water and then finely grinding the mixture by a wet grinding method.

Formulations are obtained by carrying out the same operations as those described above using metrafenone, cyflufenamid, quinoxyfen or proquinazid instead of pyriofenone.

Formulation Example 2

A formulation is obtained by mixing 10 parts of the present compound (I), 5 parts of pyriofenone, 1.5 parts of sorbitan trioleate, and 28 parts of an aqueous solution containing 2 parts of polyvinyl alcohol, finely grinding the mixture by a wet grinding method, then adding thereto 45.50 parts of an aqueous solution containing 0.05 parts of xanthan gum and 0.1 parts of aluminum magnesium silicate, further adding 10 parts of propylene glycol, and then stirring and mixing.

Formulations are obtained by carrying out the same operations as those described above using metrafenone, cyflufenamid, quinoxyfen or proquinazid instead of pyriofenone.

Formulation Example 3

A formulation is obtained by well grinding and mixing 10 parts of the present compound (I), 40 parts of pyriofenone, 3 parts of calcium lignosulfonate, 2 parts of sodium lauryl sulfate, and 45 parts of synthetic hydrated silicon dioxide.

Formulations are obtained by carrying out the same operations as those described above using metrafenone, cyflufenamid, quinoxyfen or proquinazid instead of pyriofenone.

Test examples are given below.

Test Example 1

A plastic pot was stuffed with a sand soil. Wheat (Shirogane) was sown thereon, allowed to grow in a greenhouse at 24° C. for 7 days, transferred to a greenhouse at 15° C., and then allowed to grow for 14 days. A water-diluted solution of the present compound (I) and a water-diluted solution of pyriofenone, metrafenone, cyflufenamid, quinoxyfen or proquinazid were mixed to prepare an agent solution containing prescribed amounts of the present compound (I) and, pyriofenone, metrafenone, cyflufenamid, quinoxyfen or proquinazid. The agent solution was sprayed to the foliage of the wheat, then the plant was air-dried, and then a powdery mildew was inoculated. After the inoculation, the plant was allowed to stand at 21° C. for 7 days and then an onset area rate was examined visually and a control value was calculated using the following formula.

Moreover, the present compound (I), pyriofenone, metrafenone, cyflufenamid, quinoxyfen or proquinazid was diluted with water to prepare water-diluted solutions with a prescribed concentration, the same test was carried out for each of the solutions and control values were calculated.

Control value (%)=100×(A−B)/A

A: an onset area rate of the non-treated group
B: an onset area rate of the treated group Results are shown in Table 1.

TABLE 1

| Agent | Treatment concentration (ppm) | Control value |
| --- | --- | --- |
| Present compound (I) | 0.1 | 3 |
| Metrafenone | 0.15 | 71 |
| Pyriofenone | 0.15 | 69 |
| Cyflufenamid | 0.15 | 52 |
| Quinoxyfen | 0.15 | 71 |
| Proquinazid | 0.15 | 74 |
| Present compound (I) + Metrafenone | 0.1 + 0.15 | 97 |
| Present compound (I) + Pyriofenone | 0.1 + 0.15 | 94 |
| Present compound (I) + Cyflufenamid | 0.1 + 0.15 | 87 |
| Present compound (I) + Quinoxyfen | 0.1 + 0.15 | 94 |
| Present compound (I) + Proquinazid | 0.1 + 0.15 | 90 |

The invention claimed is:

1. A plant disease control composition comprising a compound represented by formula (I) and at least one compound selected from Group A,

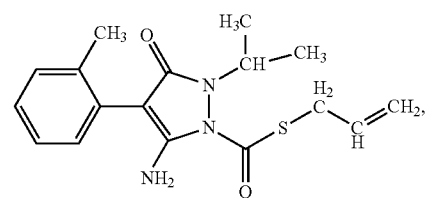

(I)

wherein Group A is selected from the group consisting of metrafenone, cyflufenamid, quinoxyfen, and proquinazid, provided that the plant disease control composition does not comprise pyriofenone.

2. The plant disease control composition according to claim 1, wherein the weight ratio of the compound represented by formula (I) to the at least one compound selected from Group A is from 100:1 to 1:100.

3. The plant disease control composition according to claim 1, wherein the at least one compound selected from Group A is metrafenone.

4. The plant disease control composition according to claim 1, wherein the at least one compound selected from Group A is cyflufenamid.

5. The plant disease control composition according to claim 1, wherein the at least one compound selected from Group A is quinoxyfen.

6. The plant disease control composition according to claim 1, wherein the at least one compound selected from Group A is proquinazid.

7. A method for controlling a plant disease, the method comprising a step of applying effective amounts of a compound represented by formula (I) and at least one compound selected from Group A to a plant, a seed of a plant, or a soil where a plant is to be cultivated,

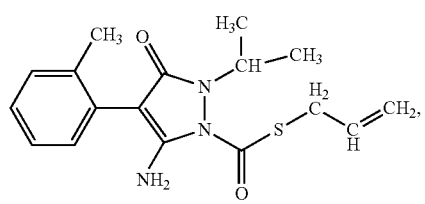

(I)

wherein Group A is selected from the group consisting of metrafenone, cyflufenamid, quinoxyfen, and proquinazid, provided that the method does not comprise applying an effective amount of pyriofenone.

8. The plant disease control composition according to claim 2, wherein the at least one compound selected from Group A is metrafenone.

9. The plant disease control composition according to claim 2, wherein the at least one compound selected from Group A is cyflufenamid.

10. The plant disease control composition according to claim 2, wherein the at least one compound selected from Group A is quinoxyfen.

11. The plant disease control composition according to claim 2, wherein the at least one compound selected from Group A is proquinazid.

12. The method according to claim 7, wherein the at least one compound selected from Group A is metrafenone.

13. The method according to claim 7, wherein the at least one compound selected from Group A is cyflufenamid.

14. The method according to claim 7, wherein the at least one compound selected from Group A is quinoxyfen.

15. The method according to claim 7, wherein the at least one compound selected from Group A is proquinazid.

* * * * *